United States Patent
Watanabe et al.

(10) Patent No.: US 9,737,690 B2
(45) Date of Patent: Aug. 22, 2017

(54) DUAL PURPOSE BALLOON CATHETERS

(71) Applicants: Gwendolyn Watanabe, Los Altos Hills, CA (US); Jeffrey A. Krolik, Campbell, CA (US)

(72) Inventors: Gwendolyn Watanabe, Los Altos Hills, CA (US); Jeffrey A. Krolik, Campbell, CA (US)

(73) Assignee: Teleflex Medical Incorporated, Research Triangle Park, NC (US)

(*) Notice: Subject to any disclaimer, the term of this patent is extended or adjusted under 35 U.S.C. 154(b) by 477 days.

(21) Appl. No.: 13/644,022

(22) Filed: Oct. 3, 2012

(65) Prior Publication Data

US 2014/0094777 A1 Apr. 3, 2014
US 2016/0271372 A9 Sep. 22, 2016

Related U.S. Application Data

(60) Provisional application No. 61/626,711, filed on Oct. 3, 2011.

(51) Int. Cl.
*A61M 25/10* (2013.01)
*A61M 29/02* (2006.01)
*A61M 25/00* (2006.01)

(52) U.S. Cl.
CPC .......... *A61M 25/10* (2013.01); *A61M 25/104* (2013.01); *A61M 25/1011* (2013.01); *A61M 29/02* (2013.01); *A61M 25/007* (2013.01); *A61M 25/10181* (2013.11); *A61M 2025/109* (2013.01); *A61M 2025/1015* (2013.01); *A61M 2025/1052* (2013.01); *A61M 2025/1093* (2013.01)

(58) Field of Classification Search
CPC  A61M 25/1011; A61M 25/10; A61M 25/104; A61M 29/02; A61M 2025/1052; A61M 2025/1093; A61M 25/10181; A61M 25/007; A61M 25/1018; A61M 2025/105; A61M 2025/109; A61M 2025/1015
USPC ... 604/95.03, 96.01, 101.01, 101.03, 101.05, 604/102.01, 102.03, 103.06, 604/103.08–103.09, 101.04
See application file for complete search history.

(56) References Cited

U.S. PATENT DOCUMENTS

| | | | |
|---|---|---|---|
| 5,163,906 A * | 11/1992 | Ahmadi | A61M 25/1011 604/101.03 |
| 6,547,754 B1 | 4/2003 | Evans et al. | |
| 6,569,146 B1 * | 5/2003 | Werner | A61B 17/22 604/101.01 |
| 8,821,476 B2 | 9/2014 | Agah et al. | |

(Continued)

OTHER PUBLICATIONS

Merriam-Webster Dictionary definition for "Adjacent", available online as of Mar. 5, 2016 at http://www.merriam-webster.com/dictionary/adjacent.*

*Primary Examiner* — Theodore Stigell
*Assistant Examiner* — Amber Stiles
(74) *Attorney, Agent, or Firm* — Baker & Hostetler LLP (57) ABSTRACT

Enhanced dual purpose systems enable dilating of at least a lesion within a blood vessel and providing an anti-proliferative medicament in a non-attached form directly into the lumen of the vessel. Likewise provided is the ability to stop blood flow to prevent wash-out of the medicament during dwell time within the body lumen, and the ability to remove the medicament after the dwell time of the device to prevent unwanted exposure of the same within the body.

11 Claims, 5 Drawing Sheets

(56) References Cited

U.S. PATENT DOCUMENTS

| | | | |
|---|---|---|---|
| 2001/0023333 A1* | 9/2001 | Wise | A61M 25/003 604/101.01 |
| 2002/0065507 A1* | 5/2002 | Zadno-Azizi | A61B 17/12022 604/509 |
| 2005/0038383 A1 | 2/2005 | Kelley et al. | |
| 2005/0124844 A1* | 6/2005 | Forman | 600/3 |
| 2005/0245894 A1* | 11/2005 | Zadno-Azizi | A61B 17/12045 604/509 |
| 2006/0129093 A1* | 6/2006 | Jackson | A61B 17/320725 604/96.01 |
| 2006/0212022 A1* | 9/2006 | Gellman | 604/509 |
| 2006/0259005 A1* | 11/2006 | Konstantino et al. | 604/500 |
| 2009/0018486 A1* | 1/2009 | Goren et al. | 604/21 |
| 2010/0036410 A1* | 2/2010 | Krolik | A61B 17/22032 606/194 |
| 2010/0082012 A1* | 4/2010 | Hattangadi et al. | 604/509 |
| 2012/0259215 A1* | 10/2012 | Gerrans | A61M 25/1011 600/435 |
| 2014/0276135 A1 | 9/2014 | Agah et al. | |
| 2016/0015948 A1 | 1/2016 | Agah et al. | |
| 2016/0082178 A1 | 3/2016 | Agah et al. | |

* cited by examiner

FIG. 8B

DUAL PURPOSE BALLOON CATHETERS

RELATED APPLICATIONS

This application claims full Paris Convention Priority of U.S. Provisional Application No. 61/626,711, entitled "Dual Purpose Balloon Catheter," which was filed on Oct. 3, 2011, the contents of which are incorporated by reference herein, as if fully set forth in its entirety. Likewise incorporated by reference is co-pending U.S. Utility application Ser. No. 13/216,208, including common inventors with the instant filing.

FIELD OF THE DISCLOSURES

Lesions within body lumens may occur within the body and prevent proper function of that body lumen. In the case of blood vessels, the lesion may prevent adequate blood flow to support downstream tissues. In this event, it is common procedure to access the lesion through a percutaneous approach and expand the lesion using a high-pressure balloon. This approach typically has a good initial result, but the lesion may re-stenos, requiring re-treatment of the lesion site. Many devices have recently addressed the re-stenosis issue through the delivery of anti-proliferative drugs such as paxitaxel, sirolimus, zotarolimus, everolimus, or others by providing the drug either on an implantable stent, or more recently, on the external surface of a balloon. What is needed is effective devices for dilating the lesion and providing an anti-proliferative drug in a non-attached form directly into the lumen of the vessel. Nothing in the art effectively offers the ability to stop blood flow to prevent wash-out of the drug during its dwell time within the body lumen, and the ability to remove the drug after the dwell time of the drug to prevent unwanted exposure of the drug within the body.

OBJECTS AND SUMMARY OF THE DISCLOSURE

Briefly stated, enhanced dual purpose systems enable dilating of at least a lesion within a blood vessel and are effective for providing an anti-proliferative medicament in a non-attached form directly into the lumen of the vessel. Likewise provided is the ability to stop blood flow to prevent wash-out of the medicament during dwell time within the body lumen, and the ability to remove the medicament after the dwell time of the device to prevent unwanted exposure of the same within the body.

According to embodiments, there is provided a method for treating a patient, comprising the steps of providing a catheter having an elongate, flexible body, a first lumen, a second lumen and an inflatable balloon; advancing the balloon to a desired site in a vessel; inflating the balloon by introducing inflation media through the first lumen; and, infusing fluid into the vessel outside of the catheter and adjacent the balloon by infusing the fluid through the first lumen.

According to embodiments, there is provided a method of imaging target vasculature, comprising the steps of advancing a balloon catheter along a guidewire to position the balloon at a desired site, the balloon catheter comprising an inflation lumen and a guidewire lumen; inflating the balloon at the site; infusing contrast media adjacent the balloon; and; visualizing the contrast media; wherein the contrast media is infused through the inflation lumen.

According to embodiments, there is provided a method for treating a body lumen of a patient using a balloon apparatus comprising an outer member including a first lumen extending between proximal and distal ends thereof, an inner member slidable within the first lumen, a balloon attached to a distal end of the inner member beyond the outer member distal end, the method comprising: introducing the distal end of the outer member into a body lumen with the balloon in a contracted condition and the inner member in a proximal position such that a sealing member on the inner member substantially seals an outlet in the outer member distal end communicating with the first lumen; directing an actuator on a proximal end of the apparatus to move the inner member to a distal position consequently directing the sealing member away from the outlet; delivering fluid through the first lumen such that the fluid passes through the outlet into the body lumen; directing the inner member towards the proximal position to substantially seal the outlet with the sealing member such that one or more passages in the sealing member communicate between the first lumen and an interior of the balloon; and, delivering fluid through the first lumen with the outlet substantially sealed, thereby delivering fluid through the one or more passages into the balloon interior to expand the balloon from the contracted condition to an enlarged condition.

According to embodiments, there is provided a medical device system, comprising, in combination, a pressurized balloon adopted for inflation and deflation between an expanded diameter and a collapsed configuration; wherein mounting of the balloon on a catheter system is defined by the addition of an anti-infective agent upon the balloon during the collapsed configuration; and, the balloon is equipped with such anti-infective agent, whereby allowing release of the anti-infective agent during inflation and deflation of the balloon.

DETAILED DESCRIPTION OF THE FIGURES

The present inventors have discovered, with enhanced balloons and valving improvements, a treatment system for use on lesions within a body lumen.

Lesions within body lumens may occur within the body and prevent proper function of that body lumen. In the case of blood vessels, the lesion may prevent adequate blood flow to support downstream tissues. In this event, it is common procedure to access the lesion through a percutaneous approach and expand the lesion using a high-pressure balloon. This approach typically has a good initial result, but the lesion may re-stenos, requiring re-treatment of the lesion site. Many devices have recently addressed the re-stenosis issue through the delivery of anti-proliferative drugs such as paxitaxel, sirolimus, zotarolimus, everolimus, or others by providing the drug either on an implantable stent, or more recently, on the external surface of a balloon. The simple elegance of the present device serves to accomplish the same goal of dilating the lesion and providing an anti-proliferative drug in a non-attached form directly into the lumen of the vessel. The device includes the ability to stop blood flow to prevent wash-out of the drug during its dwell time within the body lumen, and the ability to remove the drug after the dwell time of the drug to prevent unwanted exposure of the drug within the body. A further description is shown in the following Figures, whereby common reference designating elements are arrayed to the extent possible, with normal substitutions as would be known to artisans alternately explored.

Figure 1:
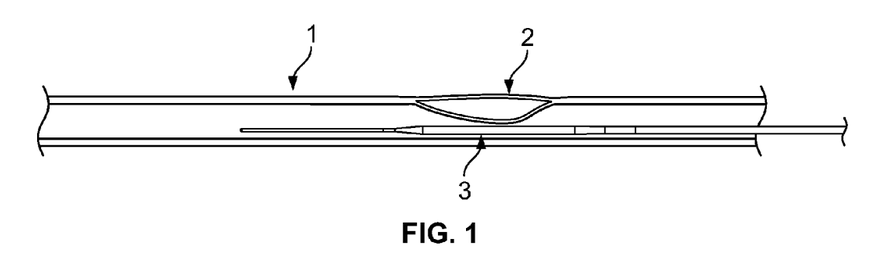
FIG. 1 shows an illustrative exemplary schematic according to the instant inventions.

Referring now to FIG. 1, a body lumen (1) has a lesion (2) that is obstructing blood flow. An interventional device is introduced and balloon (3) is centered within the lesion. Those of skill in the art readily understand techniques for imaging, location of lesions, and thus, such details are omitted at this time, as further explained by the documents incorporated by reference herein.

Figure 2:
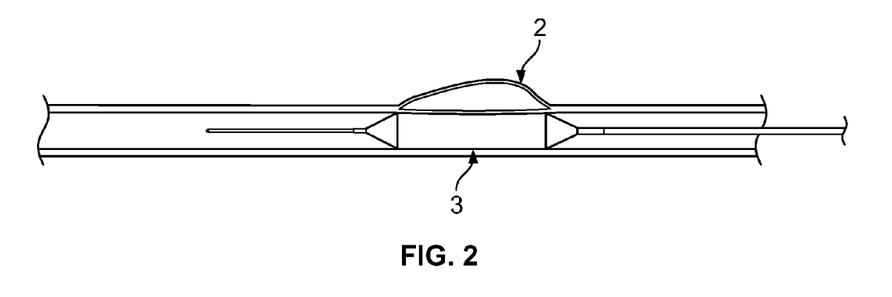
FIG. 2 shows an illustrative exemplary schematic according to the instant inventions.

Referring now to FIG. 2, a balloon (3) is inflated to expand the lesion (2). Once again, those skilled in the art readily import all needed pressures and indications for such procedures, mindful that compliant, non-compliant and extremely high-pressure balloons, up to greater than 30 atmospheres, may sometimes be used.

Figure 3:
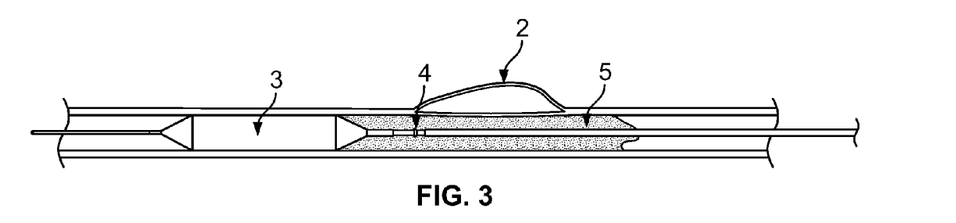
FIG. 3 shows an illustrative exemplary schematic according to embodiments of the instant inventions.

Referring now to FIG. 3, with lesion (2) dilated, balloon (3) may be advanced to a location distal to the lesion and re-inflated to a low pressure that is sufficient to block blood flow, but not expand or damage the body lumen. Valve (4) may then be opened as discussed in provisional applications contained in the set of U.S. provisional Ser. Nos. 61/153,620; 61/214,667; 61/215,732; 61/271,627; 61/283,035; 61/342,755; 61/397,854; 61/402,166; 61/463,537; and 61/520,927, each of which is incorporated expressly by this reference, as if fully set forth herein. Valve (4) allows the user to inject anti-proliferative drugs/medicaments (5) into the body lumen, where they may dwell for a period of time to allow them to take effect on dilated stenosis and adjacent tissues. Once the dwell time is finished, the user may elect to aspirate the drug out of the patient through the valve to prevent undesired exposure of the drug to other body tissues once the balloon is deflated and removed. By injecting the anti-proliferative drug after lesion expansion, it may have a more direct access to stenosed tissue by virtue of the fissures in the vessel wall created during lesion expansion. This more direct access may improve the efficacy of the anti-proliferative drug. In an alternative method of use, the balloon may be advanced distal to the lesion, and the anti-proliferative drug administered as described above prior to expansion of the lesion. This method may be used in locations where exposure of the drug to the fissures created during lesion expansion has a deleterious effect. Likewise those skilled in the art understand other drug-delivery modalities, from eluting to scoring, may be used to administer medicaments to patients according to the instant teachings.

Figure 4:
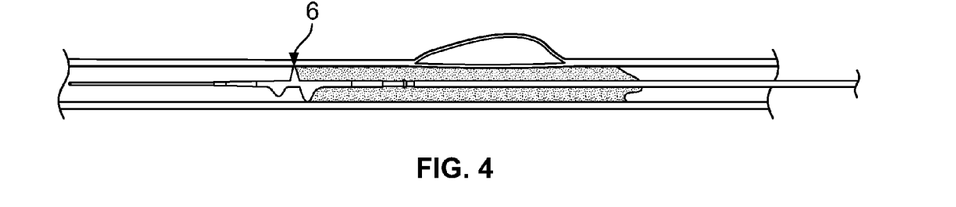
FIG. 4 shows an illustrative exemplary schematic according to embodiments of the instant inventions.
Figure 9:
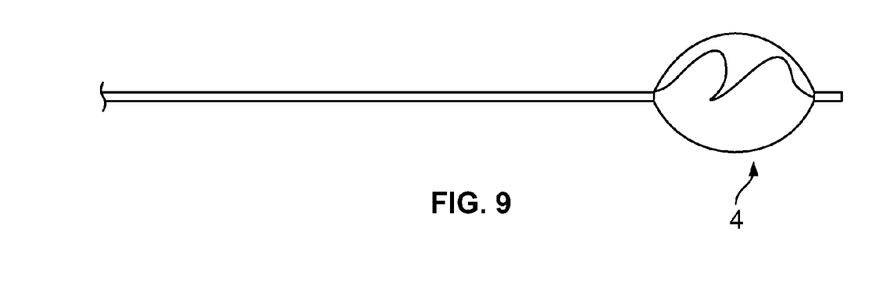
FIG. 9 demonstratively shows alternate schematic balloon structures, according to the instant inventions.
Figure 10:
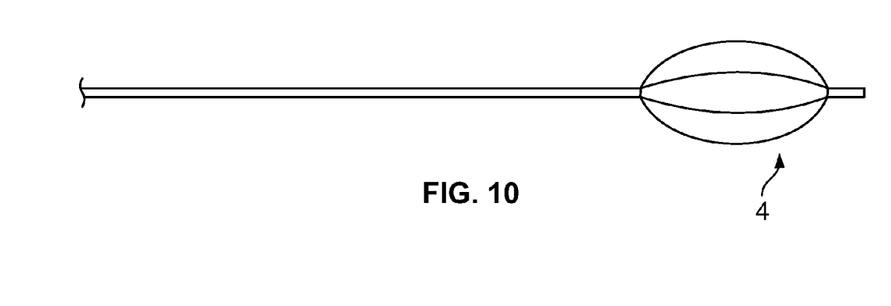
FIG. 10 demonstratively shows alternate schematic balloon structures, according to the instant inventions.
Figure 11:
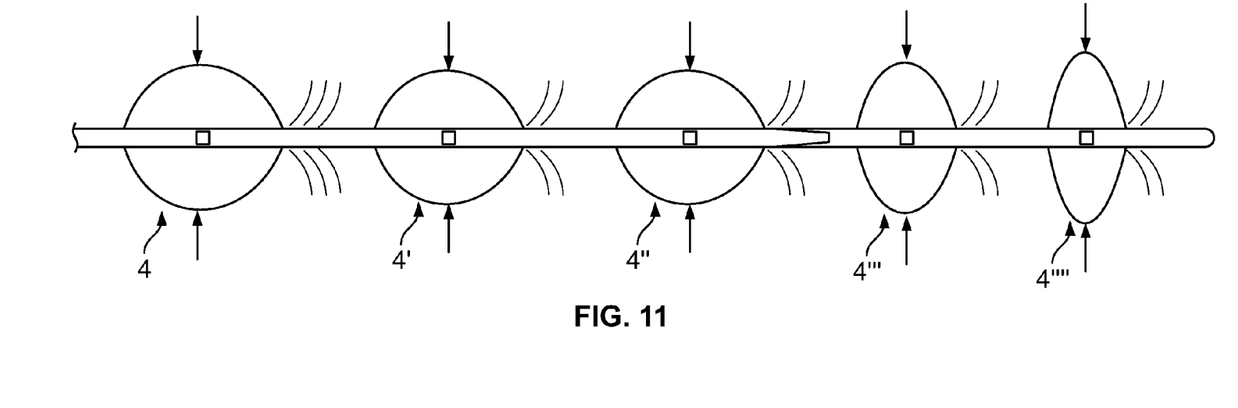
FIG. 11 demonstratively shows alternate schematic balloon structures, according to the instant inventions.

Referring now to FIG. 4, an alternative embodiment to the device is shown, where a coil (6) exists within the balloon that can be expanded, as known to those of skill in the art (see also FIGS. 9-11). The device would be used in a similar manner as described in FIG. 3, where the lesion is expanded with a balloon. During the injection of a drug, however, instead of using an inflated balloon, the coil is expanded within the vessel to cause blockage of flow within the vessel. The valve would function the same as described in FIG. 3 and the drug injection and removal could be performed before or after lesion expansion, depending on desired clinical needs.

Figure 5A:
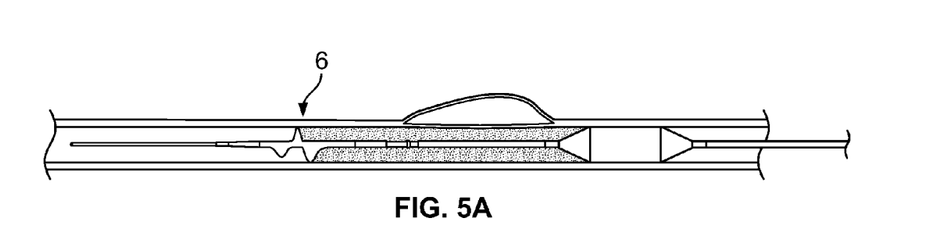
FIGS. 5A-5B show illustrative exemplary schematics according to embodiments of the instant inventions.
Figure 5B:
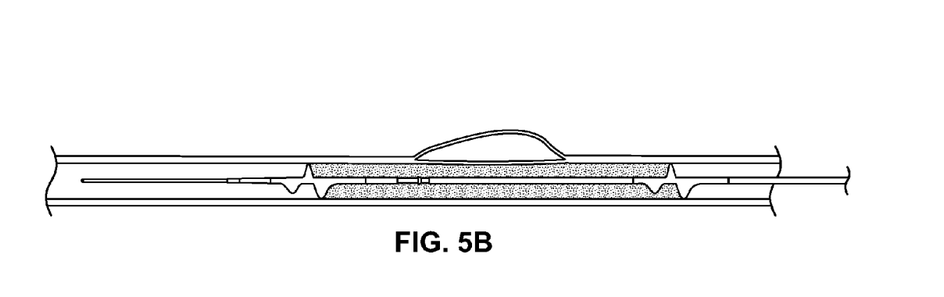

Referring now to FIG. 5, illustrated are further embodiments of the devices according to the instant teachings, where two lumen blocking structures exist to control the position of the, for example, injected anti-proliferative drug at both its distal and proximal extremities in the vessel. FIG. 5A has expanded coil (6) within the distal balloon and proximal inflated balloon (3). FIG. 5B has distal expanded coil within distal balloon (6) and proximal expanded coil (6) contained within a membrane that may be inflatable as a balloon, or may not be inflatable.

Figure 6:
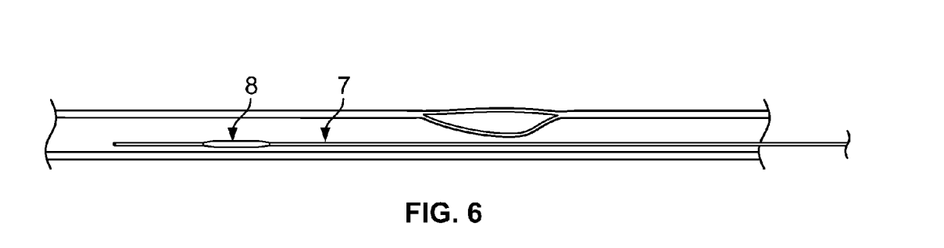
FIG. 6 shows an illustrative exemplary schematic according to the instant inventions.

Referring now to FIG. 6, this figure shows a further embodiment of an exemplary device and its method of use. In this case, guidewire (7) is used to cross the lesion. The guidewire has balloon (8) on its distal end.

Figure 7:
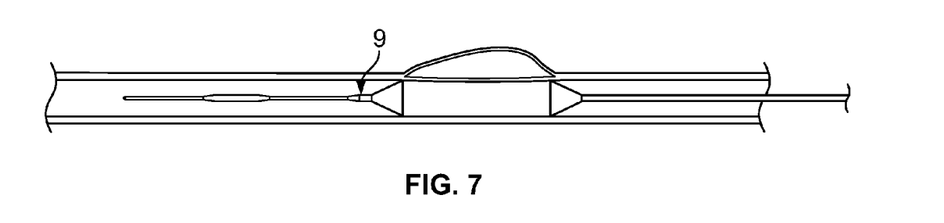
FIG. 7 shows an illustrative exemplary schematic according to the instant inventions.
Figure 8A:
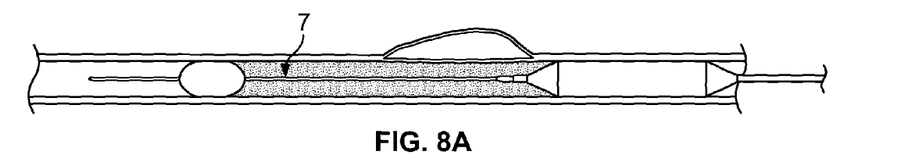
FIGS. 8A-8B show illustrative exemplary schematics according to the instant inventions.
Figure 8B:
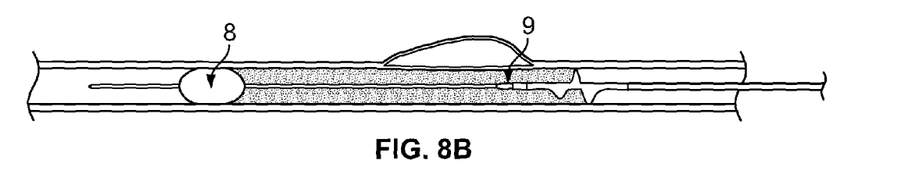

Referring now to FIG. 7 and FIG. 8, balloon catheters having distal valves (9) are tracked over the guidewire and the balloon catheter is inflated to expand the lesion, dilate, deliver drugs/medicaments as discussed.

FIGS. 8A and 8B illustrate how guidewire balloon (8) is expanded to obstruct flow in the distal direction. The balloon catheter is moved proximal to the lesion and the balloon is expanded to obstruct flow on the proximal side of the lesion. In the case of FIG. 8A, the balloon is inflated. In the case of FIG. 8B, a coil within the balloon is expanded to obstruct flow. Distal valve (9) is then opened to inject the anti-proliferative drug. After a sufficient dwell time, the drug can be aspirated back out via the open valve.

Likewise, referring to FIGS. 9-11, several alternative configurations allow for infusion, perfusion and elution of drugs, medicaments, and drug-like delivery of targeted therapies.

FIG. 9 shows RAMBO-style balloon-assembly with infusion port of valve 4, while FIG. 10 is a ribbed version, and FIG. 11 shows a series of balloon-like structures and multiple valves/ports. Those skilled in the art readily understand numerous procedures and methods to use the instant system to deliver drugs, contrast and other fluid-based matters.

In an alternative method of use, the guidewire balloon and balloon catheter may be expanded prior to lesion dilation in cases where exposure of the drug to expansion-created fissures in the vessel due to expansion is not desired. The lesion may then be expanded after drug exposure, as used according to the instant system.

Referring still to FIG. 1-FIG. 11, those skilled in the art understand catheter emplacement, the Seldinger technique and required system elements.

While the method and apparatus have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

It should also be understood that a variety of changes may be made without departing from the essence of the invention. Such changes are also implicitly included in the description. They still fall within the scope of this invention. It should be understood that this disclosure is intended to yield a patent covering numerous aspects of the invention both independently and as an overall system and in both method and apparatus modes.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these.

Particularly, it should be understood that as the disclosure relates to elements of the invention, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this invention is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all references listed in the Information Disclosure Statement or other information statement filed with the application are hereby appended and hereby incorporated by reference; however, as to each of the above, to the extent that such information or statements incorporated by reference might be considered inconsistent with the patenting of this/these invention(s), such statements are expressly not to be considered as made by the applicant.

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. A method for treating a patient, the method comprising:
providing an elongate member comprising a first inflatable balloon on a distal end of the elongate member;
advancing the elongate member within a vessel of the patient until the first inflatable balloon is distal of a desired site within the vessel;
providing a catheter comprising an elongate, flexible body, an inflation lumen, a valve in fluid communication with the inflation lumen, and a second inflatable balloon proximal of the valve;
advancing the catheter over the elongate member within the vessel of the patient until the second inflatable balloon overlaps with the desired site within the vessel;
introducing inflation media through the inflation lumen to inflate the second inflatable balloon to dilate the desired site within the vessel;
deflating the second inflatable balloon;
retracting the catheter over the elongate member within the vessel of the patient until the second inflatable balloon is proximal of the desired site within the vessel;
inflating the first inflatable balloon to obstruct distal flow in the vessel;
introducing the inflation media through the inflation lumen to re-inflate the second inflatable balloon to obstruct proximal flow in the vessel;
opening the valve to infuse fluid into the vessel between the first inflatable balloon and the second inflatable balloon;
closing the valve for a predetermined time period while the fluid is within the vessel; and
opening the valve following the predetermined time period to aspirate the fluid from within the vessel.

2. The method of claim 1, wherein said fluid comprises at least an anti-proliferative compound.

3. The method of claim 1, wherein the second inflatable balloon comprises a coil.

4. The method of claim 1, wherein the fluid comprises a contrast media.

5. The method of claim 1, wherein the fluid comprises a drug, a medicament or a therapeutic medium.

6. The method of claim 1, wherein the fluid comprises a thrombolytic agent.

7. The method of claim 1, wherein the second inflatable balloon comprises supplemental elution/deposition and scoring mechanisms disposed within or upon the second inflatable balloon.

8. The method of claim 1, wherein the valve is on an outer surface of the inflation lumen.

9. The method of claim 1, wherein the first inflatable balloon comprises a coil.

10. The method of claim 1, wherein the elongate member is a guidewire.

11. The method of claim 1, further comprising deflating the second inflatable balloon following aspiration of the fluid from within the vessel.

* * * * *